United States Patent [19]

Roberts et al.

[11] Patent Number: 4,771,037

[45] Date of Patent: Sep. 13, 1988

[54] N-CARBOXYALKYL COMPOUNDS

[75] Inventors: Richard A. Roberts, Bear, Del.; Andrew Shaw, Kennett Square, Pa.

[73] Assignee: ICI Americas Inc., Wilmington, Del.

[21] Appl. No.: 2,811

[22] Filed: Jan. 13, 1987

[30] Foreign Application Priority Data

Jan. 21, 1986 [GB] United Kingdom ................. 8601637

[51] Int. Cl.⁴ ........................ A61K 37/02; C07K 5/08
[52] U.S. Cl. ...................................... 514/18; 530/331; 530/323
[58] Field of Search ....................... 530/800, 323, 331; 514/20, 18

[56] References Cited

U.S. PATENT DOCUMENTS

| 4,374,829 | 2/1983 | Harris et al. | 530/800 |
| 4,511,504 | 4/1985 | McCullagh et al. | 560/29 |
| 4,568,666 | 2/1986 | McCullagh et al. | 514/20 |

OTHER PUBLICATIONS

Chem. Abstr. vol. 107 (1987), 33148.
Proc. of the Soc. for Exper. Biol. and Med. 183, 262–267, (1986).

*Primary Examiner*—Delbert R. Phillips
*Attorney, Agent, or Firm*—Rosemary M. Miano

[57] ABSTRACT

The invention provides a series of novel N-carboxyalkyl-peptides of formula I which are useful as inhibitors of proteoglycanase.

11 Claims, No Drawings

N-CARBOXYALKYL COMPOUNDS

BACKGROUND OF THE INVENTION

The present invention comprises certain N-carboxyalkylpeptides as inhibitors of proteoglycanase.

Selected carboxyalkyl dipeptide derivatives have been suggested as angiotension converting enzyme (ACE) inhibitors as may be seen in U.S. Pat. No. 4,472,380 to Harris et al. Selected carboxyalkyl peptides have also been suggested as collagenase inhibitors as may be seen in European Patent Application No. 84104614.7 (Publication No. 0 126 974). Neither of these documents, however, discloses compounds which are selective as proteoglycanase inhibitors and not active as collagenase inhibitors.

SUMMARY OF THE INVENTION

The compounds of this invention are selected N-carboxyalkyl di-, tri- and tetrapeptides which are useful as selective inhibitors of proteoglycanase. Such inhibitory activity may be useful whenever it is desired to inhibit the activity of proteoglycanase and, in particular, when it is desired to selectively inhibit the activity of proteoglycanase in the presence of collagenase.

DETAILED DESCRIPTION OF THE INVENTION

The invention relates to N-carboxyalkyl peptides of formula I:

(Formula set out on pages following Examples)    I where A is selected from a group consisting of —$NHR^6$, —$OCH_2R^6$, and groups represented by formulae Ia–Id:

$$-\overset{}{N}-\overset{*}{C}H-\overset{}{C}-NHR^6 \quad \text{Ia}$$
$$\quad H \quad | \quad \|$$
$$\quad\quad R^4 \quad O$$

$$-\overset{}{N}-\overset{*}{C}H-\overset{}{C}-N-\overset{*}{C}H-\overset{}{C}-NHR^6 \quad \text{Ib}$$
$$\quad H \quad | \quad \| \quad | \quad | \quad \|$$
$$\quad\quad R^4 \quad O \quad H \quad R^5 \quad O$$

$$-\overset{}{N}-\overset{*}{C}H-\overset{}{C}-OCH_2R^6 \quad \text{Ic}$$
$$\quad H \quad | \quad \|$$
$$\quad\quad R^4 \quad O$$

$$-\overset{}{N}-\overset{*}{C}H-\overset{}{C}-N-\overset{*}{C}H-\overset{}{C}-OCH_2R^6 \quad \text{Id}$$
$$\quad H \quad | \quad \| \quad | \quad | \quad \|$$
$$\quad\quad R^4 \quad O \quad H \quad R^5 \quad O$$

and where $R^1$ is selected from a group consisting of (4–6C)alkyl;
$R^2$ is selected from a group consisting of (4–6C)alkyl;
$R^3$ is selected from a group consisting of (1–6C)alkyl and (6–10C)aryl optionally substituted with a (1–4C)alkyl or a (1–4C)heteroalkyl having one or more heteroatoms independently selected from oxygen, sulfur and nitrogen;
$R^4$ is selected from a group consisting of (1–4C)alkyl and (6–10C)aryl optionally substituted with a (1–4C)alkyl or a (1–4C)heteroalkyl having one or more heteroatoms independently selected from oxygen, sulfur and nitrogen, provided that if the compound of formula I is a tripeptide terminating in —$NHR^6$ then $R^4$ may not be isobutyl;
$R^5$ is selected from a group consisting of (1–4C)alkyl and (6–10C)aryl optionally substituted with a (1–4C)alkyl or a (1–4C)heteroalkyl having one or more heteroatoms independently selected from oxygen, sulfur and nitrogen, provided that if the compound of formula I is a tetrapeptide terminating in —$NHR^6$ then $R^5$ may not be isobutyl;
$R^6$ is selected from a group consisting of hydrogen, (1–10C)alkyl or (6–10C)aryl optionally substituted with a (1–4C)alkyl or a (1–4C)heteroalkyl having one or more heteroatoms independently selected from oxygen, sulfur and nitrogen,
and acid or base addition salts thereof.

All alkyls described above include straight and branched chain alkyls. Salts include pharmaceutically acceptable salts, such as those made with HCl.

Particular values for $R^1$ are isobutyl, and preferably $R^1$ should have an R configuration.

Particular values for $R^2$ are n-butyl, n-pentyl, n-hexyl and isobutyl with a preferred value being isobutyl having an S configuration.

Particular values for $R^3$ are methyl, isopropyl, isobutyl and phenylmethyl.

Particular values for $R^4$ are methyl and phenylmethyl.

A particular value for $R^5$ is methyl.

Particular values for $R^6$ are hydrogen and methyl.

It will be appreciated by those skilled in the art that certain of the compounds of this invention may contain one or more asymmetrically substitued carbon atoms, for example, a chiral center may exist at the carbon atom(s) marked with an asterisk(s) or star in formulae I, and Ia–Id. Such compounds may exist in and be isolated in optically active and racemic forms. It has been found that the activity of the individual isomers is not always the same. It is therefore preferred to utilize the more active isomer. It has also been found that mixtures of isomers may exhibit activity and such active mixtures are also included within the scope of the invention. It will be further appreciated by those skilled in the art that optically active forms may be prepared by resolution of the racemic form or by synthesis from optically active starting materials and that active compounds and mixtures may be determined by tests hereinafter described. For these compounds the L amino acids are of the S configuration.

The compounds of the invention may be prepared by either of two general methods.

(a) A suitable α-keto acid (or derivative thereof) of formula II:

(Formula set out on pages following Examples)    II where $R^7$ is selected from a group consisting of H, (1–6C)alkyl, and phenylmethyl, may undergo reductive amination with an appropriate peptide of formula III:

(Formula set out on pages following Examples)    III

This process may be conveniently carried out by condensing the two materials in a suitable solvent (e.g., methanol) in the presence of 3 Angstrom molecular sieves to allow formation of the intermediate Schiff's base. Subsequent addition of sodium cyanoborohydride (at a pH between 6 and 7) or hydrogenation using palladium on charcoal gives the desired N-carboxyalkyl peptide of formula I which may be purified by column chromatography and/or recrystallization.

(b) A peptide of formula III above may be alkylated with an α-sulfonyloxy acid derivative of formula IV:

(Formula set out on pages following Examples)  IV in a suitable solvent (e.g., $CH_2Cl_2$, $CHCl_3$, dioxane, dioxane/$CH_2Cl_2$, dioxane/DMEU) in the presence of a base (e.g., triethylamine, [1,8-bis(dimethylamino)naphthalene, N,N,N',N'-tetramethyl-1,8-naphthalenediamine] hereinafter referred to as Proton Sponge ®). Purification by column chromatography and/or recrystallization gives a compound of formula V:

(Formula set out on pages following Examples)  V which may be deprotected to afford the desired N-carboxyalkyl peptide. Preparation of the requisite α-sulfonyloxy acid derivatives of formula IV from the corresponding optically active amino acid derivative by nitrous acid deamination allows the preparation of either enantiomer. Thus, optically active N-carboxyalkyl peptides may be prepared with stereocontrol.

The peptide starting materials, e.g., L-leucyl-L-leucyl-L-alaninamide, may be made by conventional peptide synthesis techniques.

The potency of compounds of the present invention to act as inhibitors of proteoglycanase was determined by the following test.

Chondrocyte Proteoglycanase Inhibition

For this test proteoglycan-degrading enzyme activity was measured by using the proteoglycan-polyacrylamide bead assay described by Nagase et al in *Anal. Biochem.*, 107: 385–392 (1980). The proteoglycan subunits were prepared as follows: Frozen bovine nasal septum used in the preparation of the subunits was obtained from Pel-Freez Biologicals, Rogers, Arizona. Guanidine hydrochloride (grade 1) was obtained from Sigma Chemical Co., St. Louis, Missouri. Celite ® acid-washed diatomite filter aid was supplied by Johns-Manville, Denver, Colorado. All other chemicals were of reagent or the best grade available.

The proteoglycan subunit was prepared from bovine nasal cartilage according to the procedure of Hascall et al, *J. Biol. Chem.*, 244: 2384–2396(1969), as modified by Roughly et al, *J. Biol. Chem.*, 255: 217–224(1981). Briefly, the cartilage was extracted with 4M guanidine hydrochloride containing 100 mM sodium acetate, 1 mM EDTA, 5 μg pepstatin/ml, 5 mM phenanthroline, and 0.02% sodium azide and adjusted to pH 6. The extraction mixture was stirred at 4° C. for 72 hr. The extraction mixture, with 5% diatomaceous earth (Hy-Flo Celite ®), was filtered through a coarse sintered-glass funnel. Cesium chloride was added to produce a specific gravity of 1.50. This extract was then centrifuged for 16 hr at 129,000× gravity and 8° C. in a DuPont OTD 65 ultracentrifuge according to the procedure of Radhakrishnamurthy et al., *Prep. Biochem.*, 10(2): 151–159(1980). Gradient material with a specific gravity of 1.53 and greater, containing proteoglycan subunits, was retained and recentrifuged as above. Again, the gradient material with a specific gravity of 1.53 and greater was saved. The isolated proteoglycan subunits were dialized exhaustively against deionized water containing 0.02% sodium azide for 24 to 36 hr and then lyophilized.

The proteoglycan-polyacrylamide beads were prepared as described in Nagase et al., supra. The bead assay of enzyme activity was modified as follows. The assay solution in the tubes contained 100 μl enzyme preparation and 100 μl buffer (Tris HCl, pH 7.4) or inhibitor in the buffer. Incubation with the beads was carried out at 37° C. for 6 or 20 hr. The degraded proteoglycan released from the polyacrylamide beads was determined assaying 100 μl spectrophotometrically at 535 nm with dimethylmethylene blue dye as described in Farndale et al, *Conn. Tissue Res.*, 9: 247–248 (1982). Chondroitin sulfate was used as a standard. One unit of proteoglycan-degrading activity is defined as the amount of enzyme required to release 1 μg chondroitin sulfate/ml-hr at 37° C.

The following non-limiting examples are illustrative of the invention. Unless otherwise indicated:

(i) temperatures are in degrees Centigrade and procedures were carried out at room temperature, about 18°–26° C., unless otherwise indicated;

(ii) NMR spectra were determined at 250 MHz in $CDCl_3$ or DMSO-$d_6$ using tetramethylsilane (TMS) as an internal standard, and expressed as chemical shifts (delta values) in parts per million relative to TMS using the following abbreviations for designation of major peaks: s (singlet), m (multiplet), t (triplet), br (broad), d (doublet), q (quartet);

(iii) the following abbreviations have been used: g (gram), mg (milligram), l (liter), ml (milliliter), mmol (millimole), N (normal), M (molar), m.p. (melting point), min (minute), hr (hour), w (weight), v (volume), tlc (thin layer chromatography), $R_f$(relative mobility in tlc) psi (pounds per square inch), EtOAc (ethyl acetate), THF (tetrahydrofruan), MeOH (methyl alcohol), DMSO (dimethyl sulfoxide), $Et_2O$ (diethyl ether), Pd/C (palladium on charcoal catalyst), DMEU (1,3-dimethyl-2-imidazolidinone), m/e (mass to charge ratio), TFAd (deuterated trifluoroacetic acid).

In addition, chemical symbols have their usual meanings unless otherwise indicated. As a conversion factor 133.3 Pascals=1 Torr. Atmospheric pressure=101,308 Pascals=14.70 psi. Conventional abbreviations for amino acids and peptides are also used (e.g., Leu (leucine, etc.).

EXAMPLE 1

N-[1-(R)-Carboxy-3-methylbutyl]-L-leucyl-L-phenylalaninamide (Formula I, $R_1$=—$CH_2CH(CH_3)_2$, $R^2$=—$CH_2CH(CH_3)_2$, $R_3$=—$CH_2O$, A=$NHR_6$, $R_6$=H)

To a solution of trifluoromethanesulfonic acid anhydride (0.38 ml, 2.3 mmol) in dry dichloromethane (5 ml) at 0° C. was added benzyl-2-(L)-hydroxyisocaproate (0.50 g, 2.3 mmol) and Proton Sponge ® (0.49 g, 2.3 mmol) in dichloromethane (2 ml). The mixture was allowed to stir for 30 min. at 0°–10° C. To the orange mixture was added a solution of L-leucyl-L-phenylalaninamide (0.62 g, 2.2 mmol) and Proton Sponge ® (0.49 g, 2.2 mmol) in dioxane (10 ml). The reaction was allowed to stir overnight. The mixture was filtered, then concentrated. The residue obtained was purified by column chromatography (silica gel: 3% methanol/chloroform). Recrystallization from methanol/ether/hexane gave an intermediate of N-[1-(R)-carbobenzyloxy-3-methylbutyl]-L-leucyl-L-phenylalaninamide (0.7 g, 65% yield) with a m.p. of 145°–146° C.

To a solution of the above benzyl ester intermediate (0.6 g) in methanol (40 ml) was added 10% palladium on charcoal (0.1 g). The mixture was hydrogenated overnight on a Parr apparatus at about 340000 Pascals (50 psi). It was filtered through diatomaceous earth (Celite®), then concentrated to give the title compound (0.45 g, 92% yield) with a m.p. of 183°–186° C. with decomposition. $^1$H NMR (DMSOd$_6$/TFAd) 7.3–7.1 (m, 5H), 4.7–4.6 (m, 1H), 4.0–3.8 (m, 1H), 3.4–3.3 (m, 1H), 3.1–2.8 (m, 2H), 1.7–1.5 (m, 6H), 1.0–0.7 (m, 12H).

Analysis calculated for C$_{21}$H$_{33}$N$_3$O$_4$.0.75H$_2$O: C, 62.28; H, 8.59; N, 10.37. Found: C, 62.53; H, 8.23; N, 10.22.

EXAMPLE 2

N-[1-(R)-Carboxy-3-methylbutyl]-L-leucyl-L-leucyl-L-phenylalaninamide (Formula I, $R^1$=—CH$_2$CH(CH$_3$)$_2$, $R^2$=—CH$_2$CH(CH$_3$)$_2$, $R^3$=—CH$_2$CH(CH$_3$)$_2$, A=Formula Ia, $R^4$=CH$_2$O, $R^6$=H)

To a solution of trifluoromethanesulfonic acid anhydride (0.50 ml, 3.0 mmol) in dry dichloromethane (5 ml) at 0° C. was added benzyl-2-(L)-hydroxyisocaproate (0.66 g, 3.0 mmol) and Proton Sponge® (0.64 g, 3.0 mmol) in dichloromethane (2 ml). The mixture was allowed to stir for 30 min at 0°–10° C. To the orange mixture was added a solution of L-leucyl-L-leucyl-L-phenylalaninamide (1.0 g, 2.6 mmol) and Proton Sponge® (0.55 g, 2.6 mmol) in dioxane (75 ml). The reaction was allowed to stir for 48 hr. The mixture was filtered, then concentrated. The residue obtained was purified by column chromatography (silica gel: methanol/ethyl acetate/hexanes (0.1:4:6) to give N-[1-(R)-carbobenzyloxy-3-methylbutyl]-L-leucyl-L-leucyl-L-phenylalaninamide (0.46 g, 30% yield) as an intermediate.

To a solution of the benzyl ester intermediate (0.46 g) in absolute ethanol (30 ml) was added 10% palladium on charcoal (0.11 g). The mixture was hydrogenated overnight on a Parr apparatus at about 340000 Pascals (50 psi). It was filtered through diatomaceous earth (Celite®), then concentrated. Recrystallization from methanol/ether/hexanes gave the title compound (0.36 g, 92% yield) with a m.p. of 188°–190° C. and a m/e of 505. $^1$H NMR (DMSOd$_6$/TFAD) 7.3–7.1 (m, 5H), 4.6–4.4 (m, 2H), 4.0–3.9 (m, 1H), 3.5–3.4 (m, 1H), 3.1–2.7 (m, 2H), 1.8–1.4 (m, 9H), 1.0–0.7 (m, 18H).

Analysis calculated for C$_{27}$H$_{44}$N$_4$O$_5$0.5H$_2$O: C, 63.13; H, 8.83; N, 10.91. Found: C, 63.29; H, 8.56; N, 10.70.

EXAMPLE 3

N-[1-(R)-Carboxy-3-methylbutyl]-L-leucyl-L-leucyl-L-leucyl-L-alaninamide (Formula I, $R^1$=—CH$_2$CH(CH$_3$)$_2$, $R^2$=CH$_2$CH(CH$_3$)$_2$, $R^3$=—CH$_2$CH(CH$_3$)$_2$, A=Formula Ib, $R^4$=CH$_2$CH(CH$_3$)$_2$, $R^5$=CH$_3$, $R^6$=H)

To a solution of trifluoromethanesulfonic acid anhydride (0.5 ml, 3.0 mmol) in dry dichloromethane (5 ml) at 0° C. was added benzyl-2-(L)-hydroxyisocaproate (0.66 g, 3.0 mmol) and Proton Sponge® (0.65 g, 2.3 mmol) in dichloromethane (2 ml). The mixture was allowed to stir for 30 min at 0°–10° C. To the orange mixture was added a solution of L-leucyl-L-leucyl-L-leucyl-L-alaninamide (0.90 g, 2.1 mmol) and 30 Proton Sponge® (0.46 g, 2.1 mmol) in dioxane (30 ml). The reaction was allowed to stir overnight. The mixture was filtered, then concentrated. The residue obtained was purified by medium pressure liquid chromatography (silica gel: 3% methanol/chloroform) to give N-[1-(R)-carbobenzyloxy-3-methylbutyl]-L-leucyl-L-leucyl-L-phenylalaninamide (0.9 g, 64% yield) as an intermediate.

Analysis calculated for C$_{34}$H$_{57}$N$_5$O$_6$.0.67H$_2$O: C, 63.43; H, 9.13; N, 10.88. Found: C, 63.26; H, 9.02: N, 10.52.

To a solution of the above benzyl ester intermediate (0.9 g) in methanol (75 ml) was added 10% palladium on charcoal (0.1 g). The mixture was hydrogenated overnight on a Parr apparatus at about 340000 Pascals (50 psi). It was filtered through diatomaceous earth (Celite®), then concentrated to give the title compound (0.70 g, 96% yield), with a m.p. of 175°–180° C. with decomposition. $^1$H NMR (DMSOd$_6$/TFAD) 4.6–4.5 (m, 1H), 4.4–4.3 (m, 1H), 4.2–4.1 (m, 1H), 4.0–3.9 (m, 1H), 3.5–3.4 (m, 1H), 1.8–1.4 (m, 12H), 1.2 (d, J=8 Hz, 3H), 1.0–0.7 (m, 12H).

EXAMPLE 4

N-[1-(R)-Carboxy-3-methylbutyl]-L-leucyl-L-valyl-L-phenylalaninamide (Formula I, $R^1$=—CH$_2$CH(CH$_3$)$_2$, $R^2$=—CH$_2$CH(CH$_3$)$_2$, $R^3$=—CH(CH$_3$)$_2$, A=Formula Ia, $R^4$=CH$_2$O, $R^6$=H)

To a solution of trifluoromethanesulfonic acid anhydride (0.36 ml, 2.2 mmol) in dry dichloromethane (5 ml) at 0° C. was added benzyl-2-(L)-hydroxyisocaproate (0.48 g, 2.2 mmol) and Proton Sponge® (0.45 g, 2.1 mmol) in dichloromethane (2 ml). The mixture was allowed to stir for 30 min at 0°–10° C. To the orange mixture was added a solution prepared by dissolving L-leucyl-L-valyl-L-phenylalaninamide (0.65 g, 1.7 mmol) and Proton Sponge® (0.36 g, 1.7 mmol) in DMEU (8 ml) followed by dilution with dioxane (50 ml). The reaction was allowed to stir for 5 days. The mixture was filtered, then concentrated. The residue was taken up in dioxane and slowly added to 2N HCl (200 ml) whereupon an immediate precipitate formed. The precipitate was collected by filtration, washed successively with water and dried under high vacuum to give N-[1-(R)-carbobenzyloxy-3-methylbutyl]-L-leucyl-L-valyl-L-phenylalaninamide (0.63 g, 63% yield) as an intermediate.

The benzyl ester intermediate (0.23 g) was dissolved in methanol (80 ml) and 10% palladium on charcoal (0.1 g) was added. The mixture was hydrogenated overnight on a Parr apparatus at about 340000 Pascals (50 psi). It was filtered through diatomaceous earth (Celite®), then concentrated to give the title compound with a m.p. of 196°–200° C. $^1$H NMR (DMSOd$_6$/TFAd) 7.3–7.1 (m, 5H), 4.6–4.5 (m, 1H), 4.3–4.2 (m, 1H), 4.1–4.0 (m, 1H), 3.6–3.4 (m, 1H), 3.1–2.7 (m, 2H), 2.2–1.3 (m, 7H), 1.0–0.6 (m, 18H).

Analysis calculated for C$_{26}$H$_{42}$N$_4$O$_5$.1.0H$_2$O: C, 61.39; H, 8.72; N, 11.01. Found: C, 61.39; H, 8.72; N, 10.63.

EXAMPLE 5

N-[1-(R)-Carboxy-3-methylbutyl]-L-leucyl-L-leucyl-L-alaninamide (Formula I, $R^1$=—CH$_2$CH(CH$_3$)$_2$, $R^2$=—CH$_2$CH(CH$_3$)$_2$, $R^3$=—CH$_2$CH(CH$_3$)$_2$, A=Formula Ia, $R^4$=—CH$_3$, $R^6$=H)

To a solution of trifluoromethanesulfonic acid anhydride (0.75 ml, 4.5 mmol) in dry dichloromethane (10 ml) at 0° C. was added benzyl-2-(L)-hydroxyisocaproate (0.99 g, 4.5 mmol) and Proton Sponge® (0.96 g, 4.5 mmol) in dichloromethane (3 ml). The mixture was allowed to stir for 30 min at 0°–10° C. To the orange mixture was added a solution of L-leucyl-L-leucyl-L- alaninamide (1.0 g, 3.2 mmol), Proton Sponge ® (0.68 g, 3.2 mmol) in dioxane (70 ml). The reaction was allowed to stir overnight. The mixture was filtered, then concentrated. The residue obtained was purified by column chromatography (silica gel: 3% methanol/chloroform). Recrystallization from methanol/ether/hexanes gave N-[1-(R)-carbobenzyloxy-3-methylbutyl]-L-leucyl-L-leucyl-L-alaninamide (0.91 g, 55% yield), with a m.p. of 133°-134° C. as an intermediate.

To a solution of the above benzyl ester intermediate (0.8 g) in methanol (100 ml) was added 10% palladium on charcoal (0.1 g). The mixture was hydrogenated overnight on a Parr apparatus at about 340000 Pascals (50 psi). It was filtered through diatomaceous earth (Celite ®), then concentrated. Recrystallization from methanol/ether/hexane gave the title compound (0.59 g, 89% yield), with a m.p. of 221-225° C. $^1$H NMR (DMSOd$_6$/ TFAd) 4.4–4.6 (m, 1H) 4.2–4.3 (m, 1H), 3.9–4.1 (m, 1H), 3.5–3.6 (m, 1H), 1.5–1.8 (m, 9H), 1.2 (d, 3H, J=8 Hz), 0.6–1.0 (m, 18H).

Analysis calculated for $C_{21}H_{40}N_4O_5 \cdot 2H_2O$: C, 54.29; H, 9.55; N, 12.06. Found: C, 54.47; H, 9.19; N, 12.07.

EXAMPLE 6

N-[1-(R,S)-Carboxy-3-methylbutyl]-L-leucyl-L-leucyl-L-leucyl-methyl ester (Formula I, R$^1$=—CH$_2$CH(CH$_3$)$_2$, R$^2$=—CH$_2$CH(CH$_3$)$_2$, R$^3$=—CH$_2$CH(CH$_3$)$_2$, A=Formula Ic, R$_4$=—CH$_2$CH(CH$_3$)$_2$, R$_6$=H)

To a solution of 4-methyl-2-oxo-pentanoic acid (0.75 g, 5.7 mmol) and L-leucyl-L-leucyl-L-leucine (0.95 g, 2.7 mmol) in absolute ethanol (50 ml) was added N-methylmorpholine (0.9 ml, 8.2 mmol). A white precipitate was formed. After stirring for 1 hr at room temperature, 3 Angstrom molecular sieves (3.0 g) was added. Stirring was continued for an additional 3 hr before addition of sodium cyanoborohydride (0.17 g, 2.7 mmol). The resulting mixture was stirred overnight followed by addition of another equivalent of sodium cyanoborohydride (0.17 g, 2.7 mmol). Stirring was continued for an additional 2 days. The mixture was filtered, then concentrated in vacuo. The residue was absorbed onto Amberlite ™ IRA-118H acidic cation exchange resin (100 ml) by stirring overnight in 1:1 methanol/water (500 ml). The neutrals were eluted with 1:1 methanol/water (1.5 l). The column was then eluted with 1:1 methanol/water containing 2% ammonium hydroxide (1.5 l). The solution was concentrated and the residue further purified by flash chromatography (silica gel/0.5% acetic acid, 7.5% methanol, 50% ethyl acetate, 42% hexanes) to give the title compound (0.5 g) with an R$_f$ of 0.4, 0.5 respectively in the same solvent mixture. The title product was further purified by recrystallization (ethyl acetate/hexanes) to give 0.34 g with a melting point of 137°-140° C. and a m/e of 486, 440, 341, 313, 245. $^1$H NMR (DMSOd$_6$/TFAd) 4.6–4.5 (m, 1H), 4.4–4.2 (m, 1H), 4.1–3.9 (m, 1H), 3.6 (s, 3H), 3.5–3.3 (m, 1H), 1.8–1.4 (m, 12H), 1.0–0.7 (m, 24H).

Analysis calculated for $C_{25}H_{47}N_3O_6 \cdot 1.0H_2O$: C, 59.62; H, 9.81; N, 8.34. Found: C, 59.36; H, 9.45; N, 8.07.

EXAMPLES 7-18

The procedures as exemplified in Examples 2 and 4 were repeated to make compounds with substituents and stereochemistry as listed in Table I. The procedure of Example 2 was used with appropriate substitutions of materials for all the examples in Table I except for Example 8 which was prepared by the method of Example 4. Information on stereochemistry is listed in sequence of R groups starting with R$^1$. Melting points are in degrees Centigrade.

TABLE I

| Example Number | R$^1$ | R$^2$ | R$^3$ | A | R$^4$ | R$^5$ | R$^6$ | Stereochemistry R$^1$...R$^n$ | Melting Point |
|---|---|---|---|---|---|---|---|---|---|
| 7 | isobutyl | isobutyl | isobutyl | Formula Ib | isobutyl | —CH$_2\phi$ | H | RSSSS | 209–213 |
| 8 | isobutyl | isobutyl | isobutyl | Formula Ia | (indol-3-ylmethyl) | — | H | RSSS | 143–147 |
| 9 | n-butyl | isobutyl | isobutyl | Formula Ia | —CH$_2\phi$ | — | H | RSSS | 184–187 |
| 10 | n-butyl | isobutyl | —CH$\phi$ | NHR$^2$ | — | — | H | RSS | 189–191 |
| 11 | isobutyl | n-butyl | isobutyl | Formula Ia | —CH$_2\phi$ | — | H | RSSSS | 215–218 |
| 12* | isobutyl | n-pentyl | isobutyl | Formula Ia | —CH$_2\phi$ | — | H | R(R or S)SS | 198–200 |
| 13** | isobutyl | n-hexyl | isobutyl | Formula Ia | —CH$_2\phi$ | — | H | R(R or S)SS | 180–184 |
| 14 | isobutyl | isobutyl | isobutyl | Formula Ia | —CH$_2\phi$ | — | H | SSSS | 252–255 |
| 15 | isobutyl | isobutyl | —CH$_2\phi$ | NHR$^6$ | — | — | CH$_3$ | RSS | 115–120 |
| 16 | isobutyl | isobutyl | isobutyl | Formula Ia | —CH$_2\phi$ | — | CH$_3$ | RSSSS | 167–172 |
| 17 | isobutyl | isobutyl | isopropyl | Formula Ia | —CH$_2\phi$ | — | H | SSSS | 248–250 |
| 18 | isobutyl | isobutyl | isobutyl | Formula Ia | —CH$_2\phi$ | — | H | RRSS | 126–128 |

*The other isomer is not very active and is characterized by a m.p. of 253–255° C.
**The other isomer is not very active and is characterized by a m.p. of 244–245° C.

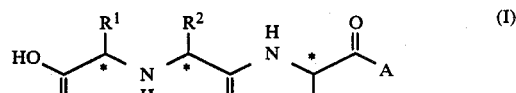

(I)

(II)

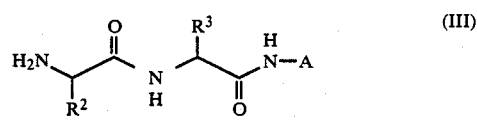

(III)

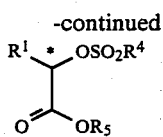

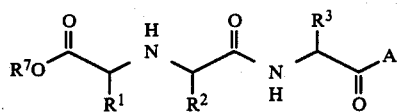

What is claimed is:
1. A compound of formula I

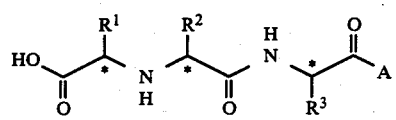

where A is selected from a group consisting of groups represented by formulae Ib and Id:

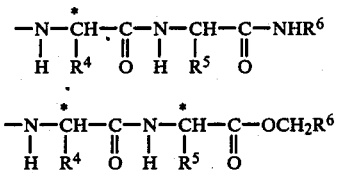

and where
R¹ is selected from a group consisting of (4–6C)alkyl;
R² is selected from a group consisting of (4–6C)alkyl;
R³ is selected from a group consisting of (1–6C)alkyl and (6–10C)aryl optionally substituted with a (1–4-C)alkyl or a (1–4C)heteroalkyl having one or more heteroatoms independently selected from oxygen, sulfur and nitrogen;
R⁴ is selected from a group consisting of (1–4C)alkyl and (6–10C)aryl optionally substituted with a (1–4-C)alkyl or a (1–4C)heteroalkyl having one or more heteroatoms independently selected from oxygen, sulfur and nitrogen, provided that if the compound of formula I is a tripeptide terminating in —NHR⁶ then R⁴ may not be isobutyl;
R⁵ is selected from a group consisting of (1–4C)alkyl and (6–10C)aryl optionally substituted with a (1–4-C)alkyl or a (1–4C)heteroalkyl having one or more heteroatoms independently selected from oxygen, sulfur and nitrogen, provided that if the compound of formula I is a tetrapeptide terminating in —NHR⁶ then R⁵ may not be isobutyl;
R⁶ is selected from a group consisting of hydrogen, (1–10C)alkyl or (6–10C)aryl optionally substituted with a (1–4C)alkyl or a (1–4C) heteroalkyl having one or more heteroatoms independently selected from oxygen, sulfur and nitrogen and acid; and
acid and base addition salts thereof.

2. A compound as claimed in claim 1 wherein R¹ is isobutyl.

3. A compound as claimed in claim 1 wherein R² is n-butyl, n-pentyl, n-hexyl or isobutyl.

4. A compound as claimed in claim 3 wherein R² is isobutyl and R² has an S configuration.

5. A compound as claimed in claim 1 wherein R³ is methyl, isopropyl, isobutyl or phenyl-methyl.

6. A compound as claimed in claim 1 wherein R⁴ is methyl or phenylmethyl.

7. A compound as claimed in claim 1 wherein R⁵ is methyl.

8. A compound as claimed in claim 1 wherein R⁶ is hydrogen or methyl.

9. A compound as claimed in claim 1 wherein A is of formula Ib, R¹, R², R³ and R⁴ are each isobutyl, R⁵ is —CH₂O and R⁶ is H.

10. A pharmaceutical composition comprising a compound of claim 1 or a pharmaceutically acceptable salt thereof in an amount sufficient to inhibit the activity of proteoglycanase in association with a non-toxic pharmaceutically acceptable diluent or carrier.

11. A method of inhibiting the activity of proteoglycanase comprising administering to a mammal a pharmaceutically effective amount of a compound of claim 1.

* * * * *

UNITED STATES PATENT AND TRADEMARK OFFICE
CERTIFICATE OF CORRECTION

PATENT NO. : 4,771,037

DATED : SEPTEMBER 13, 1988

INVENTOR(S) : ROBERTS ET AL

It is certified that error appears in the above-identified patent and that said Letters Patent is hereby corrected as shown below:

<u>In The Specification:</u>

Column 4, line 46, "$R_3=-CH_2O$," should read --$R_3=-CH_2\emptyset$,--.

Column 5, line 15, "$R^4CH_2O$" should read --$R^4=CH_2\emptyset$,--.

Column 5, line 62, "and 30 Proton" should read --and Proton--.

Column 6, line 13, "$(DMSOd_6/TFAD)$" should read --$(DMSOd_6/TFAd)$--.

Column 6, line 22, "$R^4=CH_2O$" should read --$R^4=CH_2\emptyset$--.

Table I, entry 10, columns 4 & 5, "$-CH\emptyset \quad NHR^2$ should read -- $-CH_2\emptyset \quad NHR^6$--

<u>In The Claims:</u>

Claim 9, column 10, line 33, "$-CH_2O$" should read -- $-CH_2\emptyset$--.

Signed and Sealed this

Eighteenth Day of April, 1989

*Attest:*

DONALD J. QUIGG

*Attesting Officer*  *Commissioner of Patents and Trademarks*